United States Patent
Ramaekers (12)

(10) Patent No.: US 6,506,413 B1
(45) Date of Patent: Jan. 14, 2003

(54) COMPOSITIONS FOR TREATING ANIMAL DISEASES AND SYNDROMES

(76) Inventor: Joseph C. Ramaekers, 555 Charlson Rd., Aptos, CA (US) 95003

(*) Notice: Subject to any disclaimer, the term of this patent is extended or adjusted under 35 U.S.C. 154(b) by 0 days.

(21) Appl. No.: 09/847,036

(22) Filed: Apr. 30, 2001

(51) Int. Cl.[7] .................. A61K 35/20; A61K 35/14; A61K 31/00
(52) U.S. Cl. ................ 424/535; 424/529; 424/93.51; 424/93.45; 424/600; 514/168; 514/52; 514/167; 514/251; 514/276; 514/458; 514/474; 514/725
(58) Field of Search ................ 424/535, 529, 424/520, 582, 93.51, 93.45, 725, 780, 195.16, 931.1, 600; 514/168, 52, 167, 251, 276, 458, 474, 725

(56) References Cited

U.S. PATENT DOCUMENTS

| 4,435,384 A | * | 3/1984 | Warren |
| 4,816,563 A | * | 3/1989 | Wilson et al. |
| 5,234,698 A | * | 8/1993 | Fahim |
| 5,840,700 A | * | 11/1998 | Kirkpatrick et al. |

* cited by examiner

*Primary Examiner*—Leon B. Lankford, Jr.
*Assistant Examiner*—Ruth Davis
(74) *Attorney, Agent, or Firm*—Richard F. Trecartin; Dorsey & Whitney LLP

(57) ABSTRACT

Various compositions containing transfer factor in combination with nutraceuticals are provided including transfer factor in combination with zinc and essential fatty acids and transfer factor in combination with lactic acid generating bacteria. Also provided are methods for treating animal diseases and syndromes using these compositions.

6 Claims, No Drawings

COMPOSITIONS FOR TREATING ANIMAL DISEASES AND SYNDROMES

FIELD OF THE INVENTION

This invention relates to compositions of transfer factor in combination with specific nutraceuticals and to the use of these compositions in treating diseases and syndromes.

BACKGROUND OF THE INVENTION

Transfer factor which is produced by leucocytes and lymphocytes are small water soluble polypeptides of about eight amino acids and also associated cofactors that stimulate or transfer cell mediated immunity from one individual to another and across species. Since transfer factors are smaller than antibodies, they do not transfer antibody mediated responses nor do they induce antibody production. The properties, characteristics and processes for obtaining transfer factor or transfer factors are discussed in U.S. Pat. Nos. 4,816,563; 5,080,895; 5,840,700 and 5,883,224, the contents of which are hereby incorporated by reference into the present application. Transfer factor has been described as an effective therapeutic for Herpes simplex virus (Viza, et al.), a treatment for acne blemishes, U.S. Pat. No. 4,435,384 and as a treatment against *C. albicans* (Khan et al.). Transfer factor has also been used to treat intestinal cryptosporidiosis in recipients treated with specific transfer factor (McMeeking, et al.). Still, et al. also showed that chicken pox infections were prevented by pretreatment of children treated with transfer factor from individuals that had chicken pox or who in other words had been sensitized to the varicella antigen. It may be assumed that the individual or animal that is the source of the transfer factor has been sensitized to the antigen of interest. The term antigen is defined herein is anything that will initiate the cell mediated immune response. However, transfer factor as found in commercial bovine colostrum extract coming from a pool of animals (e.g., cows) contains the acquired immunity from all of the pool and therefore provides a type of generalized adoptive transfer of immunity. Transfer factors or transfer factor can be obtained from a dialyzable extract of the lyzed cells or from an extract of extracellular fluid containing transfer factor. Common sources of transfer factors are colostrum, ova, blood and milk. It is common practice to refer to preparations that contain transfer factor by the name of the active component (i.e., transfer factor). Transfer factor extract containing transfer factors is also herein referred to as transfer factor. Transfer factor from bovine colostrum extract is defined as defatted water soluble material from colostrum that will pass through a nominal 10,000 molecular weight filter.

The use of nutraceuticals to treat vitamin and mineral deficiencies is well known. However, the use of nutraceuticals, such as vitamins, minerals and other nutritional components to prevent and treat diseases other than those caused by the deficiency of those nutraceuticals, though still controversial, is receiving more consideration from both laymen and physicians. The following is a list of nutraceuticals and some of their generally acknowledged nutritional and health benefits.

Vitamin A—is important in preventing eye epithileol disorders; deficiency results in night blindness Vitamin $B_2$—is essential to human nutrition relating to the oxidation of carbohydrates and amino acids Mixed tocopherols—are antioxidants Choline Chloride—is a member of the vitamin B complex and a dietetic factor for furnishing free methyl groups for transmethylation Vitamin $B_6$—functions in the formation and breakdown of amino acids and is involved in the synthesis of serotonin and norepinephrine. However, exact dietary requirements are uncertain Vitamin $B_{12}$—is an antipernicious-anemia factor essential for normal hemopoiesis Vitamin E—is an antioxidant that protects against free radicals.

Vitamin K—is essential for the formation of prothrombin

Biotin—functions in metabolic processes leading to the formation of fats and utilization of carbon dioxide Folic Acid—a growth factor involved in the formation of nucleic acids and necessary for the formation of heme Niacin—a component of the Vitamin B complex, a deficiency results in pellagra Vitamin $D_3$—is important in the absorption of calcium Pantothenic Acid—is considered essential for growth and well being of animals; deficiency results in growth retardation, skin lesions and graying of hair Thiamine—is necessary in diet of all animals except ruminants; used to prevent beriberi and important in carbohydrate metabolism Lysine—is an essential amino acid Methionine—is a sulfur containing essential amino acid Arginine—is an amino acid important in the synthesis of urea (principal form in which mammals excrete)

Soy—is a source of proteins

Methyl Sulfonyl Methane—is a form of organic sulfur involved in cell membrane permeability Zinc—is an essential mineral for growth; deficiency creates susceptibility to various pathogens Omega 3-, 6-, and 9-Fatty Acids—are essential fatty acids and polyunsaturated fats; a deficiency results in hypertension and high blood pressure; they are believed to improve immune function Yeast—(e.g., brewers, bakers, etc.) contains beta glucans which appear to increase production and/or activation of natural killer cells Calcium—is required for bone development Phosphorus—is required for bone development Selenium—a deficiency results in heart muscle disease Iron—is required for formation of hemoglobin; deficiency results in anemia Magnesium—is an element required for growth in all living organisms Manganese—is an element required for growth in all living organisms Copper—is an element required for growth in plants, animals and most microorganisms Iodine—is an element necessary for the synthesis of hormone production by the thyroid gland Cobalt—is a trace element essential in the nutrition of ruminants (cattle, sheep) and in the maturation of human red blood cells in the form of Vitamin $B_{12}$ Molybdenum—is a trace element believed to be necessary in animal diets but its function in the minimal levels have not been established Lactic Acid Generating Bacteria—are a digestive aid and growth inhibitor of harmful bacteria Chrondroitin—is a component of connective tissue which may relieve joint pain and arthritis.

Glucosamine—is a component of micropolysaccharides and glycoprotein which may be helpful in arthritis.

Di-methyl glycine—is a methylated amino acid found in all cells and an antioxidant.

Montmorillonite—is collodial clay containing trace elements which are considered by some to be important for well being and to compensate for elements no longer in foods because of depleted soils (the components are shown below in Table 1)

TABLE 1

Montmorillonite Components
Average Nutrient Content Per Ounce
(1 Tablespoon = 0.36 oz.)
(mg)

| | | | |
|---|---|---|---|
| Silicon | 6933 | Tungsten | 0.218 |
| Aluminum Silica | 2505 | Vanadium | 0.215 |
| Sodium Chloride | 1320 | Ruthenium | 0.210 |
| Potassium | 1293 | Baron | 0.189 |
| Protein | 1116 | Bromine | 0.140 |
| Calcium | 1104 | Cobalt | 0.129 |
| Sulfur | 431 | Selenium | 0.110 |
| Iron | 431 | Syprosium | 0.107 |
| Magnesium | 224 | Fluorine | 0.102 |
| Chlorine | 164 | Scandium | 0.0997 |
| Titanium | 61.9 | Samarium | 0.0943 |
| Carbon | 48.2 | Nobelium | 0.0754 |
| Sodium | 37.2 | Copper | 0.0593 |
| Barium | 10.5 | Praseodymium | 0.0539 |
| Phosphate | 8.62 | Erbium | 0.0539 |
| Strontium | 6.46 | Hafnium | 0.0539 |
| Cesium | 4.93 | Ytterbium | 0.0377 |
| Manganese | 4.04 | Lithium | 0.0377 |
| Thorium | 2.69 | Yttrium | 0.0323 |
| Uranium | 2.69 | Holmium | 0.0296 |
| Arsenic | 1.97 | Cadmium | 0.0296 |
| Chromium | 1.89 | Palladium | 0.0189 |
| Molybdenum | 1.64 | Terbium | 0.0161 |
| Nickel | 1.62 | Thulium | 0.0161 |
| Iodine | 1.28 | Gold | 0.0161 |
| Lead | 1.17 | Tantalum | 0.0135 |
| Cerium | 1.08 | Iridium | 0.0135 |
| Rubidium | 0.983 | Lutetium | 0.0108 |
| Antimony | 0.781 | Europium | 0.0108 |
| Gallium | 0.673 | Rhodium | 0.0108 |
| Germanium | 0.673 | Tin | 0.0108 |
| Neodymium | 0.539 | Silver | 0.00808 |
| Zinc | 0.539 | Indium | 0.00808 |
| Lanthanum | 0.486 | Oxygen | 0.00539 |
| Bismuth | 0.385 | Mercury | 0.00269 |
| Zirconium | 0.269 | Tellurium | 0.00269 |
| Rhenium | 0.269 | Beryllium | 0.00269 |
| Thallium | 0.269 | | |

Allopathic medicine is usually used to treat animal diseases. Unfortunately, such medicines often have serious side effects such as nausea, gastritis, diarrhea, maladsorption of vitamins, circulation and respiratory problems and allergic reactions. For example, Cushings disease, a fairly common physiological abnormality in ungulates, particularly horses, manifests itself as a pituitary adenoma that results in erratic cortisol and insulin levels. Cushings syndrome, however, is defined as a cortisol excess regardless of the cause. Clinical signs are frequent urination, polydypsia, failure to shed hair and poor hair coat, lack of muscle tone and sometimes poor coordination. The common allopathic drugs for treating Cushings disease and/or Cushings syndrome are Parlodel (bromocreptine mesylate) a dopamine agonist, cyproheptadine a serotonin blocker, and Permax (pergolide mesylate) another dopamine agonist. However, in oral form Parlodel has poor absorption and the intra molecular injectible form which needs to be given twice a day is impractical. Cyproheptadine usually takes about six to eight weeks and since it is a serotonin antagonist it can effect other systems in the brain. Permax is also an intense vasoconstrictor and can worsen chronic laminitis which is common with Cushings.

Onchocerciasis is a disease resulting from infection from microfilariae spread by flies and is characterized by fibrous nodules in the skin and subcutaneous tissues. The usual treatment is the anthelcide Ivermectin, yet the autoimmune component of this disease remains to the extent that there are constant relapses. Cortizone and antibiotics are also used. However, both of these drugs can be extremely toxic and often cause allergic reactions.

Equine protozoal myelitis that results in severe inflamation of the spinal chord or of the bone marrow is usually treated with Pyrimethamine (an antibiotic), sulfadiazine (an antibiotic) and Trimethoprim sulfur (an antibiotic). Livestock, especially horses and cows, often suffer from ulcers, including stomach ulcers and ulcerations and inflammation of the joints. The ulcers and ulcerations are usually treated with strong antibiotics and cortisones which again can cause allergic reactions, fever and other severe side effects. Also, the use of antibiotics to treat animals especially livestock food source animals often results in resistance to those antibiotics which is becoming a serious health problem with respect to all animals including humans. inflammation is usually treated with a NSAID (non-steroidal antiinflamatory drug), compositions which again sometimes have serious side effects such as kidney and liver complications.

Diseases fairly common in domestic pets are feline leukemia in a cat and flea bite dermatitis in numerous animals such as cats, dogs, etc. Feline leukemia can be treated with various current oncological drugs but they are very expensive. Treatment of flea bite dermatitis in animals usually involves antibiotics and prednisone which is often ineffective and use of prednisone can cause sodium retention, eye problems and heart failure.

Strangles, a disease in horses caused by *Streptococcus equi* that forms abscesses in the lymph nodes and other parts of the body, is usually treated by rest and antibiotic therapy. The disease spreads quickly and is difficult to prevent. The disease can also cause chronic life-long mononucleosis-like symptoms in the horse.

Many animals such as dogs and livestock (horses, cows, sheep, etc.) suffer from chronic coughs believed to be caused by dust allergens. While seldom fatal, the ailment can lead to serious complications such as secondary infections. The cough which is often confused with other upper respiratory infections is usually treated with antibiotics such as Trimethoprim sulfur and expectorants. However, such treatment is often ineffectual.

Lymphopenia and hypothyroidism also occur in livestock. Lymphopenia is a decrease in the number or proportion of lymphocytes in the circulating blood which often leads to an increased susceptibility to bacterial and fungal infections. This hematologic abnormality can result from hereditary diseases, impaired production because of bone marrow cancer, but often the result of the impairment of cell production by drugs such as cancer drugs, antithyroid drugs, phenothyoscenes, penicillin, and other antibiotics. Again, treatment usually involves broad spectrum antibiotic therapy which again can lead to antibiotic resistance or other physiological problems.

Hypothyroidism in livestock and often domestic animals frequently occurs for unknown reasons. Treatment often involves replacement therapy with synthetic preparations of thyroxine. However, long-term replacement therapy can result in heart problems and bone diseases such as osteoporosis.

Another very serious problem with farm animals is high morbidity (i.e., sickness) among young animals which can result in severe financial losses to farmers and ranchers. The current methods of controlling morbidity involve a standard oat or grain diet for livestock and fowl, and inoculations and antibiotics.

Since most of the above discussed common medical treatments can involve serious side effects, compositions containing natural products and nutraceuticals that would treat the foregoing diseases and syndromes with less contraindications and diminish the development of antibiotic resistance are highly desirable, not only to relieve suffering in the animals but also to improve the quality of meat and human health.

SUMMARY OF THE INVENTION

This invention provides formulations of transfer factor in combination with minerals, antioxidants, amino acids and other nutraceuticals preferably administered orally to treat animals exhibiting disease symptoms but also to lower general morbidity.

Accordingly, one aspect of this invention provides a formulation comprising transfer factor, zinc and at least one essential fatty acid.

A second aspect of the invention is to provide a formulation of transfer factor zinc, at least one essential fatty acid, vitamin C and yeast.

A third aspect of the invention is to provide a formulation of transfer factor zinc, at least one essential fatty acid, vitamin C, yeast, ionic salts or chelates of the elements calcium, phosphorous, selenium, iron, magnesium, manganese, copper, iodine, cobalt and molybdenum.

A fourth aspect of the invention is to provide a formulation of lactic acid generating bacteria, yeast, montmorillonite, vitamins A, $B_2$, $B_6$, $B_{12}$, E and K, biotin, folic acid, niacin, vitamin $D_3$, pantothenic acid, thiamine, lysine, methionine, arginine and methyl sulfonyl methane.

A fifth aspect of the invention is to provide a formulation comprising transfer factor, zinc, at least one essential fatty acid, vitamin C, yeast and ionic salts or chelates of the elements calcium, phosphorous, selenium, iron, magnesium, manganese, copper, iodine, cobalt and molybdenium.

Another aspect of the invention is to provide a formulation of transfer factor, zinc, at least one essential fatty acid, vitamin C, ionic salts or chelates of the elements calcium, phosphorous, selenium, iron, magnesium, manganese, copper, iodine, cobalt and molybdenum, lactic acid generating bacteria, yeast, montmorillonite, vitamins A, $B_2$, $B_6$, $B_{12}$, E and K.

A further aspect of the invention is to provide a formulation of transfer factor and lactic acid generating bacteria.

Yet another aspect of the invention is to provide a formulation of transfer factor, zinc at least one essential fatty acid, vitamin C, ionic salts or chelates of the elements calcium, phosphorous, selenium, iron, magnesium, manganese, copper, iodine, cobalt and molybdenum, lactic acid generating bacteria, yeast, montmorillonite, vitamins A, $B_2$, $B_6$, $B_{12}$, E and K, biotin, folic acid, niacin, vitamin $D_3$, pantothenic acid and thiamine.

Still another aspect of the invention is to provide a formulation comprising transfer factor, zinc, at least one essential fatty acid, vitamin C, ionic salts or chelates of the elements calcium, phosphorous, selenium, iron, magnesium, manganese, copper, iodine, cobalt and molybdenum, lactic acid generating bacteria, yeast, montmorillonite and vitamins A, $B_2$, $B_6$, $B_{12}$, E and K, and biotin, folic acid, niacin, vitamin $D_3$, pantothenic acid, thiamine, lysine, methionine, arginine, and methyl sulfonyl methane.

In yet another aspect, the invention provides the method of treating Cushing syndrome, Cushings disease, adenomas and other benign tumors, onchocerciasis or equine protozoal myelitis in an animal comprising administering to the animal a formulation of transfer factor, zinc and at least one essential fatty acid in an amount and at a frequency and for a duration effective to decrease or eliminate the tumors or the symptoms of those diseases.

A further aspect of the invention is to treat Cushing syndrome, Cushings disease, adenomas, onchocerciasis, hypothyroidism or equine protozoal myelitis by administering to the animal a formulation of transfer factor, zinc and at least one essential fatty acid in combination with nutraceuticals selected from the group consisting of vitamin C, ionic salts or chelates of the elements calcium, phosphorous, selenium, iron, magnesium, manganese, copper, iodine, cobalt and molybdenum, lactic acid generating bacteria, yeast, montmorillonite, vitamins A, $B_2$, $B_6$, $B_{12}$, E and K, and biotin, folic acid, niacin, vitamin $D_3$, pantothenic acid, lysine, methionine, arginine and methyl sulfonyl methane. The preferred formulation for treating these diseases includes all of the nutraceuticals.

Still a further aspect of the invention is a method of treating inflamation and ulcers in an animal comprising administering to the animal in an amount at a frequency and for a duration effective to reduce or eliminate the symptoms of the inflamation or ulcers a formulation comprising transfer factor and lactic acid generating bacteria.

Yet another aspect of this invention is a method of treating inflamation and ulcers in an animal comprising administering to the animal a formulation of transfer factor and other nutraceuticals selected from the group consisting of zinc, methyl sulfonyl methane, lactic acid generating bacteria, yeast, at least one essential fatty acid, vitamin C, ionic salts or chelates of the elements calcium, phosphorous, selenium, iron, magnesium, manganese, copper, iodine, cobalt and molybdenum, montmorillonite, vitamins A, $B_2$, $B_6$, $B_{12}$, E and K, and biotin, folic acid, niacin, vitamin $D_3$, pantothenic acid, thiamine, lysine, methionine and arginine and mixtures thereof in an amount, at a frequency and for a duration effective to reduce or eliminate the symptoms of the inflamation or ulcers.

Still yet another aspect of the invention provides for a formulation comprising transfer factor and a lactic acid generating bacteria.

Yet another aspect of the invention is to provide a formulation, a transfer factor, lactic acid generating bacteria and zinc.

Still a further aspect of the invention is to provide for a formulation comprising transfer factor, lactic acid generating bacteria, and montmorillonite.

Still another aspect of the invention is a formulation comprising transfer factor, lactic acid generating bacteria, zinc, montmorillonite, at least one essential fatty acid, ionic salt or chelates of the elements calcium, phosphorous, selenium, iron, magnesium, manganese, copper, iodine, cobalt and molybdenum, yeast, vitamins A, $B_2$, $B_6$, $B_{12}$, C, E and K, biotin, folic acid, niacin, vitamin $D_3$, pantothenic acid, thiamine, lysine, methionine, arginine and methyl sulfonyl methane.

Another aspect of this invention provides for a method of treating flea bite dermatitis in an animal or feline leukemia in a cat comprising administering to the animal or cat a formulation of transfer factor and lactic acid generating bacteria in an amount and at a frequency and for a duration effective to reduce or eliminate the symptoms of the dermatitis or leukemia.

Still a further aspect of the invention provides for a method of treating flea bite dermatitis in an animal or feline leukemia in a cat comprising administering to the animal or cat the formulation comprising transfer factor, lactic acid generating bacteria, zinc, montmorillonite, at least one essential fatty acid, ionic salt or chelates of the elements calcium, phosphorous, selenium, iron, magnesium, manganese, copper, iodine, cobalt and molybdenum, yeast, vitamins A, $B_2$, $B_6$, $B_{12}$, C, E and K, biotin, folic acid, niacin, vitamin $D_3$, pantothenic acid, thiamine, lysine, methionine, arginine, and methyl sulfonyl methane in an amount and at a frequency and for a duration effective to reduce or eliminate symptoms of the dermatitis or leukemia.

A further aspect of the invention is to provide a method of treating strangles, chronic dust allergen cough or hypothyroidism in an animal comprising administering to the animal a formulation of transfer factor and a lactic acid generating bacteria in an amount and at a frequency and for a duration effective to reduce or eliminate the symptoms of the strangles, chronic dust allergen cough or hypothyroidism.

Still another aspect of the invention is a method of treating lymphopenia in an animal comprising administering to the animal a formulation of transfer factor and a lactic acid generating bacteria in an amount, at a frequency and for a duration effective to reduce or eliminate the symptoms of the lymphopenia.

Still a further aspect of the invention is a method of reducing morbidity in young livestock animals comprising administering to the animals a formulation of transfer factor and a lactic acid generating bacteria in a amount, at a frequency and for a duration effective to achieve a reduction in morbidity as compared to controls.

Yet another aspect of the invention is to provide a formulation comprising transfer factor, lactic acid generating bacteria, ionic salts or chelates of the elements calcium, magnesium, sodium and potassium, citric acid, vitamins A, $B_2$, $B_6$, $B_{12}$, C and E, and yeast.

Still another aspect of this invention is a method of treating strangles, chronic dust allergen cough or hypothyroidism in an animal comprising administering to the animal a formulation of transfer factor and lactic acid generating bacteria and other nutraceuticals selected from the group consisting of ionic salts or chelates of the elements calcium, magnesium, sodium and potassium, citric acid, vitamins A, $B_1$, $B_2$, $B_6$, $B_{12}$, C and E, and yeast. The preferred formulation comprises transfer factor, lactic acid generating bacteria and all of these other nutraceuticals.

Yet a further aspect of the invention is a method of treating lymphopenia in an animal comprising administering to the animal a formulation of transfer factor and lactic acid generating bacteria and other nutraceuticals selected from the group consisting of ionic salts or chelates of the elements calcium, magnesium, sodium, potassium and zinc, citric acid, vitamins A, $B_1$, $B_2$, $B_6$, $B_{12}$, C and E, and yeast. The preferred formulation comprises transfer factor, a lactic acid generating bacteria and all of these other nutraceuticals.

Still yet another aspect of the invention is a method of reducing morbidity in young livestock animal comprising administering to the animals a formulation of transfer factor and lactic acid generating bacteria and nutraceuticals selected from the group consisting of ionic salts or chelates of the elements calcium, magnesium, sodium and potassium, citric acid, vitamins A, $B_1$, $B_2$, $B_6$, $B_{12}$, C and E, and yeast. The preferred formulation comprises transfer factor, a lactic acid generating bacteria and all of these other nutraceuticals.

Other aspects of the invention will become apparent to the skilled artisan by the following description of the invention.

DETAILED DESCRIPTION OF THE INVENTION

In accordance with this detailed description, the following definitions and abbreviations apply.

Nutraceuticals—Nutrients used to treat or prevent a disease or syndrome.

Pharmaceutically acceptable—meant that the substance in the dose and form given is not known to cause serious side effects and harm apart from an occasional allergic reaction. In general, as used herein, the term pharmaceutically acceptable has the same meaning as the common meaning for that term. However, the substance need not be pharmaceutically acceptable for humans unless the recipient is human. Nevertheless, it must be relatively safe for the animal receiving the substance.

EPM—Equine protozoal myelitis.

Various forms of transfer factor may be used in accordance with this invention. They include excreted transfer factor released from transfer factor containing cells such as lymphocytes and leukocytes, and collected from extracellular fluids such as colostrum, blood and milk. Another form includes preexcreted transfer factor found within the cell or on the cell surface. Also substantially pure transfer factor defined as ribonuclease resistant polyribonucleotides having a molecular weight of less than 10,000 daltons and a specific activity of at least 5000 units per adsorbance unit at 214 nM may also be used but is not necessary for the results achieved in the course of this invention. The invention may also use transfer factor specific for an antigen obtained by collecting transfer factor from an animal that has been exposed to that antigen. An example of such an antigen may be *Streptococcus equi*. The transfer factor used in the Examples of this invention and referred to in the following Tables and further referred to in the rest of the detailed description is extracted from colostrum collected from a general pool of lactating cows. The transfer factor, as used in the Examples, Tables and the following description, is further defined as defatted water soluble material from bovine colostrum that will pass through a nominal 10,000 molecular weight filter. Though bovine colostral derived transfer factor was used to develop the formulations of this invention, it is well known to anyone skilled in the art that other kinds and sources of transfer factor could be used.

Table 2, shows a breakdown of a formulation of transfer factor nutraceuticals and carriers for treating Cushing syndrome, Cushings disease, adenomas, onchocerciasis, hypothyroidism or EPM. In Table 2 and all the other tables references to "lb" (pounds) means pounds of body weight.

Columns 2, 3 and 4 of Tables 2–5 show the approximate high, low and preferred amounts, respectively, of the formulation components, in amounts per body weight, to be given to an animal in a single dosage. The formulations in Tables 3 and 4 are very similar to the formulation of Table 2 but they are specialized for dogs and cats respectively. The formulation represented in Table 2 is designed primarily for livestock. The 5 ounces of the formula listed in column 5 is designed to be given to a 1000 pound animal. The average horse is around 1000 pounds. The 28.3 gm dosage in Table 3 is calculated for a dog weighing about 100–200 pounds. The 2.2 gm formula in Table 4 is for a cat weighing around 15 pounds. However, since these formulas are comprised of nutraceuticals and transfer factor, one skilled in the art will recognize that the ranges are not as certain and as critical as the ranges for allopathic drugs.

Further, the formulations in Tables 2–4 are designed to treat mainly chronic diseases while the formulation in Table 5 is designed for mainly acute diseases and may be given in megadoses to achieve an acute response.

Administration of a formulation of transfer factor, zinc and at least one essential fatty acid will result in at least a partially effective treatment of Cushings syndrome, Cushings disease, adenomas and other benign tumors, onchocerciasis, hypothyroidism or EPM. The treatment is more effective as other nutraceuticals listed in Table 2 are added. The dosage is in milligrams per pound unless otherwise stated. The amounts of the components present in a 5 ounce formulation transfer factor containing the other preferred nutraceuticals is shown in column 5 of Table 2.

Transfer factor at a dosage of about 0.75 mg/lb in combination with about 0.49 mg/lb zinc and 20.57 mg/lb of canola oil, safflower oil or flax oil, sources of essential fatty acids (i.e., 3, 6, 9 omega fatty acids), given once daily to an animal suffering from Cushings syndrome, Cushings disease, adenomas or other benign tumors, onchocerciasis, hypothyroidism or equine protozoal myelytis will result in approximately a 30% to 50% reduction in the size of the benign tumors and/or the symptoms of these listed diseases. All of these components should of course be pharmaceutically acceptable to the animal receiving them.

A combination of Vitamin C at about 2.16 mg/lb and 2.29 mg/lb of yeast in combination with the above listed transfer factor and other fatty acid nutraceuticals will results in approximately a 40% to 50% reduction in the size of benign tumors and/or symptoms of the above listed diseases.

It is preferred in all formulations of the invention that the metal nutraceuticals are proteinated because these forms are easier for the animal to digest and also because the proteinate forms are more stable to pH. The nutraceutical components in the formulations in Tables 2–5 are the active components for treating the various described diseases and syndromes. The fillers and carriers are included to make the formulations more palatable to the animal and also to help preserve the mixture. These include silicon dioxide, maltodextrin, soy and peanut flour, peanut oil, dextrose, whey, spices and flavorings. Mixed tocopherols and choline chloride are nutraceuticals but the effective results described herein can still be achieved by deleting these two components from the formulations.

A daily dosage of 141 mg per pound of body weight of any of the formulations in column of Tables 2, 3 or 4, for 14 days has been successful in treating feline pneumonitis, feline leukemia, feline autoimmune dysfunction, feline flea bit dermatitis, feline hyperthyroidism, feline viral infection, feline ulcerations, feline bacterial infection, canine flea bite dermatitis, canine Cushings disease, canine autoimmune dysfunctiiion, canine viral and bacterial infection. These treatments for the most part have resulted in complete cures.

Administering a formulation comprising all of the nutraceuticals in Table 2 at the preferred dosage to an animal with benign tumors resulted in about a 60% reduction in the size of the benign tumors and about a 90% reduction in the symptoms exhibited by the animal suffering the above listed diseases and syndromes.

Administration of all of the nutraceuticals in Table 2 at the low dosage in column 3 of those tables results in about a 7% to 100% reduction in the size of the tumors and/or a 30% to 100% reduction in the symptoms exhibited by the animal suffering from those diseases or syndromes.

The stress formulation in Table 5 is also used to treat numerous animal diseases and syndromes and as stated previously, mainly their acute stages. This formulation is also water soluble so it can be given in the animals drinking water. A mixture of about 0.75 mg/lb transfer factor and about 1.42 mg/lb lactobacillus acidophilus $10^9$ colony forming units (CFU) given twice daily will result in at least a 30% reduction in clinical symptoms resulting from strangles, dust cough, hypothyroidism and lymphopenia. The same dosage given to young calves will also reduce morbidity by about 30%. The addition of ionic salts or chelates of calcium, magnesium sodium and potassium twice daily in amounts approximating those in column 4 of Table 5 to the above amounts of transfer factor and lactic acid generating bacterial results in a 40% reduction in clinical symptoms of the above mentioned diseases. The addition of about 0.482 mg/lb of citric acid to the above formulation results in about a 45% reduction in the symptoms of the above mentioned diseases. Further addition of Vitamins A, $B_2$, $B_6$, $B_{12}$, C and E, and thiamine results in a 50% reduction in the symptoms of these diseases. The stress formulations given twice a day in the dosage presented in column 4 of Table 5 will treat and, if not cure them, reduce the symptoms of autoimmune dust cough, diarrhea from viral etiology, abscessation, in strangles, snotty nose in strangles, acute viremia in swine, scratches in the horse, hypersensitivity from scratches and onchocerciasis, and pnemonitis in cats.

TABLE 2

Premix Formulation
(Amounts in mg/lb of body weight unless otherwise stated)

| Component | High | Low | Preferred | Dosage: mg/5 oz. of formula |
|---|---|---|---|---|
| 1-Arginine | 0.5 | 0.005 | 0.05 | 50.00 |
| *Lacto yeast (4.9% of blend) | 69.51 | 0.6951 | 6.91 | 6951.88 |
| Montmorillinite | 1 gm/lb | 0.24118 | 2.4118 | 2411.88 |
| Canola oil (14.5% mix) | 1.5 gm/lb | 2.05 | 20.571 | 20571.88 |
| Safflower oil (14.5% mix) | 1.5 gm/lb | 2.05 | 20.57 | 20571.88 |
| Flax seed oil (55% Alpha Linolenic Acid) (1.0% mix) | 1.5 gm/lb | 2.05 | 20.571 | 1418.75 |
| Phosphorous (Monosodium phosphate) 12% | 15.750 gm | 0.0525 | 5.08 | 5080.00 |
| Calcium carbonate 8.5% (38% calcium) | 13.68 gm | 0.0485 | 4.88 | 4880.00 |
| Methyl sulfonyl methane | 20 | 0.02 | 2 | 2000.00 |
| Transfer factor | 50.00 | 0.05 | 0.75 | 750.00 |
| Vitamin C (ascorbic acid) | 21.62 | 0.2162 | 2.162 | 2162.50 |
| d-Biotin (Vitamin H 2%) | 9.73 | 0.000973 | 0.00973 | 10.00 |

TABLE 2-continued

Premix Formulation
(Amounts in mg/lb of body weight unless otherwise stated)

| Component | High | Low | Preferred | Dosage: mg/5 oz. of formula |
|---|---|---|---|---|
| Vitamin $D_3$ | 29.16 IU | 0.7298 IU | 7.298 IU | 7298.38IU |
| Vitamin $B_{12}$ | 0.092 | 0.000092 | 0.00092 | 0.92 |
| Folic Acid | 1 | 0.001006 | 0.01006 | 10.06 |
| Niacinimide | 12 | 0.012157 | 0.12157 | 121.57 |
| Pantothenic acid (d-Calcium Pantothenate) 91.6% | 0.324 | 0.0108 | 0.108 | 108.00 |
| Vitamin $B_6$ (Pyridine Hcl) 82.3% | 1.158 | 0.001158 | 0.01158 | 11.58 |
| Vitamin A (Retinol Palmitate) 650M IU/g feed grade | 600 IU | 4.02 IU | 40.212 IU | 40232.50IU |
| Vitamin $B_2$ | 0.0554 | 0.002776 | 0.02776 | 27.76 |
| Thiamine (Mononitrate) 83% | 3.09 | 0.00308 | 0.0308 | 30.80 |
| Vitamin E | 72.9 IU | 0.0729 IU | 0.729 IU | 729.42IU |
| Vitamin K | 1 | 0.0007 | 0.007 | 7.00 |
| Cobalt (Proteinate) 5% | 0.00043 | 0.000043 | 0.00043 | 0.43 |
| Copper (Proteinate) 10% | 0.56 | 0.0112 | 0.112 | 112.00 |
| Iodine (Potassiumiodide) 98% | 0.005 | 0.000053 | 0.00053 | 0.53 |
| Iron (Proteinate) 15% | 3.31 | 0.0331 | 0.331 | 331.16 |
| Magnesium (Oxide) 58% | 10 | 0.04 | 0.4 | 400.00 |
| Manganese (Proeinate) 15% | 1.65 | 0.04 | 0.4 | 332.10 |
| Molybdenum (Sodium Molybdate Dihydrate) 39% | 0.05 | 0.001 | 0.01 | 10.00 |
| Selenium (Sodium Selenite) 44.8% | 0.00162 | 0.000081 | 0.00081 | 1.00 |
| Zinc (Proteinate) 15% | 50 | 0.04987 | 0.4987 | 498.72 |
| 1-Lysine (Mono HCl) | 8.41 | 0.0841 | 0.841 | 841.57 |
| d,1-Methionine | 11.03 | 0.1103 | 1.103 | 1103.86 |
| Mixed Tocopherols | | | | 300.00 |
| Choline Chloride | | | | 2434.00 |
| Sipernat 50 (Silicon dioxide) | | | | 12768.75 |
| Lodex-5 (maltodextrin) | | | | 7519.38 |
| Soy flour (17.5% mix) | | | | 24828.13 |
| Sweet whey | | | | 996.00 |
| BF70 spice | | | | 146.00 |
| Dextrose powder | | | | 750.00 |

*Lactic acid generating bacteria is two-thirds of component and yeast is one-third; lactic acid generating bacteria is 500,000,000 CFU/gm, yeast (e.g., "Saccharamyces") 250,000,000 CFU/gm

TABLE 3

Canine Premix Formulation
(Amounts in mg/lb of body weight unless otherwise stated)

| Component | High | Low | Preferred | Dosage: mg/28.37 gm of formula |
|---|---|---|---|---|
| 1-Arginine | 0.5 | 0.005 | 0.05 | 10.00 |
| *Lacto yeast (4.9% of blend) | 69.51 | 0.6951 | 6.91 | 1390.38 |
| Montmorillinite | 1 gm/lb | 0.24118 | 2.4118 | 482.20 |
| Canola oil (14.5% mix) | 1.5 gm/lb | 2.05 | 20.571 | 3887.00 |
| Safflower oil (14.5% mix) | 1.5 gm/lb | 2.05 | 20.57 | 3887.00 |
| Flax seed oil (55% Alpha Linolenic Acid) (1.0% mix) | 1.5 gm/lb | 2.05 | 20.571 | 240.00 |
| Phosphorous (Monosodium phosphate) 12% | 15.750 gm | 0.0525 | 5.08 | 1010.00 |
| Calcium carbonate 8.5% (38% calcium) | 13.68 gm | 0.0485 | 4.88 | 977.00 |
| Methyl sulfonyl methane | 20 | 0.02 | 2 | 400.00 |
| Transfer factor | 50.00 | 0.05 | 2.50 | 500.00 |
| Vitamin C (ascorbic acid) | 21.62 | 0.2162 | 2.162 | 432.50 |
| d-Biotin (Vitamin H 2%) | 9.73 | 0.000973 | 0.00973 | 2.00 |
| Vitamin $D_3$ | 29.16 IU | 0.7298 IU | 7.298 IU | 1459.68 IU |
| Vitamin $B_{12}$ | 0.092 | 0.000092 | 0.00092 | 0.18 |
| Folic Acid | 1 | 0.001006 | 0.01006 | 2.16 |
| Niacinimide | 12 | 0.012157 | 0.12157 | 24.31 |
| Pantothenic acid (d-Calcium Pantothenate) 91.6% | 0.324 | 0.0108 | 0.108 | 21.60 |
| Vitamin $B_6$ (Pyridine Hcl) 82.3% | 1.158 | 0.001158 | 0.01158 | 2.32 |

TABLE 3-continued

Canine Premix Formulation
(Amounts in mg/lb of body weight unless otherwise stated)

| Component | High | Low | Preferred | Dosage: mg/28.37 gm of formula |
|---|---|---|---|---|
| Vitamin A (Retinol Palmitate) 650M IU/g feed grade | 600 IU | 4.02 IU | 40.212 IU | 8046.50 IU |
| Vitamin B$_2$ | 0.0554 | 0.002776 | 0.02776 | 5.55 |
| Thiamine (Mononitrate) 83% | 3.09 | 0.00308 | 0.0308 | 0.16 |
| Vitamin E | 72.9 IU | 0.0729 IU | 0.729 IU | 145.88 IU |
| Vitamin K | 1 | 0.0007 | 0.007 | 1.40 |
| Cobalt (Proteinate) 5% | 0.00043 | 0.000043 | 0.00043 | 0.086 |
| Copper (Proteinate) 10% | 0.56 | 0.0112 | 0.112 | 22.40 |
| Iodine (Potassiumiodide) 98% | 0.005 | 0.000053 | 0.00053 | 0.106 |
| Iron (Proteinate) 15% | 3.31 | 0.0331 | 0.331 | 66.23 |
| Magnesium (Oxide) 58% | 10 | 0.04 | 0.4 | 80.00 |
| Manganese (Proeinate) 15% | 1.65 | 0.04 | 0.4 | 66.42 |
| Molybdenum (Sodium Molybdate Dihydrate) 39% | 0.05 | 0.001 | 0.01 | 2.00 |
| Selenium (Sodium Selenite) 44.8% | 0.00162 | 0.000081 | 0.00081 | 0.20 |
| Zinc (Proteinate) 15% | 50 | 0.04987 | 0.4987 | 99.74 |
| 1-Lysine (Mono HCl) | 8.41 | 0.0841 | 0.841 | 176.91 |
| d,1-Methionine | 11.03 | 0.1103 | 1.103 | 220.77 |
| Mixed Tocopherols | | | | 60.00 |
| Choline Chloride | | | | 486.80 |
| Sipernat 50 (Silicon dioxide) | | | | 2553.35 |
| Lodex-5 (maltodextrin) | | | | 1508.87 |
| Peanut oil | | | | 496.56 |
| Soy flour (17.5% mix) | | | | 4965.02 |
| Peanut flour | | | | 4965.02 |
| Sweet whey | | | | 400.00 |
| BF70 spice | | | | 29.20 |
| Dextrose powder | | | | 500.00 |

*Lactic acid generating bacteria is two-thirds of component and yeast is one-third; lactic acid generating bacteria is 500,000,000 CFU/gm, yeast (e.g., "Saccharamyces") 250,000,000 CFU/gm

TABLE 4

Feline Premix Formulation
(Amounts in mg/lb of body weight unless otherwise stated)

| Component | High | Low | Preferred | Dosage: mg/2.2 gm of formula |
|---|---|---|---|---|
| 1-Arginine | 0.5 | 0.005 | 0.05 | 0.78 |
| *Lacto yeast (4.9% of blend) | 69.51 | 0.6951 | 6.91 | 108.42 |
| Montmorillinite | 1 gm/lb | 0.24118 | 2.4118 | 37.00 |
| Canola oil (14.5% mix) | 1.5 gm/b | 2.05 | 20.571 | 323.25 |
| Safflower oil (14.5% mix) | 1.5 gm/lb | 2.05 | 20.57 | 323.25 |
| Flax seed oil (55% Alpha Linolenic Acid) (1.0% mix) | 1.5 gm/lb | 2.05 | 20.571 | 22.13 |
| Phosphorous (Monosodium phosphate) 12% | 15.750 gm | 0.0525 | 5.08 | 78.70 |
| Calcium carbonate 8.5% (38% calcium) | 13.68 gm | 0.0485 | 4.88 | 75.69 |
| Methyl sulfonyl methane | 20 | 0.02 | 2 | 31.20 |
| Transfer factor | 50.00 | 0.05 | 16.00 | 250.00 |
| Vitamin C (ascorbic acid) | 21.62 | 0.2162 | 2.162 | 33.73 |
| d-Biotin (Vitamin H 2%) | 9.73 | 0.000973 | 0.00973 | 0.156 |
| Vitamin D$_3$ | 29.16 IU | 0.7298 IU | 7.298 IU | 113.90 IU |
| Vitamin B$_{12}$ | 0.092 | 0.000092 | 0.00092 | 0.014 |
| Folic Acid | 1 | 0.001006 | 0.01006 | 0.168 |
| Niacinimide | 12 | 0.012157 | 0.12157 | 1.90 |
| Pantothenic acid (d-Calcium Pantothenate) 91.6% | 0.324 | 0.0108 | 0.108 | 1.68 |
| Vitamin B$_6$ (Pyridine Hcl) 82.3%) | 1.158 | 0.001158 | 0.01158 | 0.18 |
| Vitamin A (Retinol Palmitate) 650M IU/g feed grade | 600 IU | 4.02 IU | 40.212 IU | 627.60 IU |
| Vitamin B$_2$ | 0.0554 | 0.002776 | 0.02776 | 0.43 |
| Thiamine (Mononitrate) 83% | 3.09 | 0.00308 | 0.0308 | 0.48 |
| Vitamin E | 72.9 IU | 0.0729 IU | 0.729 IU | 11.38 IU |
| Vitamin K | 1 | 0.0007 | 0.007 | 0.11 |

TABLE 4-continued

Feline Premix Formulation
(Amounts in mg/lb of body weight unless otherwise stated)

| Component | High | Low | Preferred | Dosage: mg/2.2 gm of formula |
|---|---|---|---|---|
| Cobalt (Proteinate) 5% | 0.00043 | 0.000043 | 0.00043 | 0.006 |
| Copper (Proteinate) 10% | 0.56 | 0.0112 | 0.112 | 1.75 |
| Iodine (Potassiumiodide) 98% | 0.005 | 0.000053 | 0.00053 | 0.008 |
| Iron (Proteinate) 15% | 3.31 | 0.0331 | 0.331 | 5.17 |
| Magnesium (Oxide) 58% | 10 | 0.04 | 0.4 | 6.24 |
| Manganese (Proeinate) 15% | 1.65 | 0.04 | 0.4 | 5.18 |
| Molybdenum (Sodium Molybdate Dihydrate) 39% | 0.05 | 0.001 | 0.01 | 0.156 |
| Selenium (Sodium Selenite) 44.8% | 0.00162 | 0.000081 | 0.00081 | 0.156 |
| Zinc (Proteinate) 15% | 50 | 0.04987 | 0.4987 | 7.78 |
| 1-Lysine (Mono HCl) | 8.41 | 0.0841 | 0.841 | 13.80 |
| d,1-Methionine | 11.03 | 0.1103 | 1.103 | 17.22 |
| Mixed Tocopherols | | | | 4.68 |
| Choline Chloride | | | | 38.0 |
| Sipernat 50 (Silicon dioxide) | | | | 199.06 |
| Lodex-5 (maltodextrin) | | | | 117.30 |
| Sweet whey | | | | 155.37 |
| BF70 spice | | | | 2.28 |
| Dextrose powder | | | | 250.00 |
| Glucosamine HCl | | | | 100.00 |
| Pernaconniculus-Chondroitin | | | | 200.00 |

*Lactic acid generating bacteria is two-thirds of component and yeast is one-third; lactic acid generating bacteria is 500,000,000 CFU/gm, yeast (e.g., "Saccharamyces") 250,000,000 CFU/gm

TABLE 5

Stress Formula
(Amounts in mg/lb of body weight unless otherwise stated)

| Component | High | Low | Preferred | Dosage: mg/ounce of formula |
|---|---|---|---|---|
| Calcium Pantothenate | 1.80 | 0.09 | 0.028 | 28.00 |
| Vitamin C (ascorbic acid) | 20.00 | 0.056 | 0.017 | 17.00 |
| Vitamin $B_{12}$ | 13.00 | 0.13 | 0.198 | 198.59 |
| Vitamin A | 600.00 IU | 0.10 IU | 0.014 | 14.00 |
| Vitamin $B_2$ | 1.20 | 0.065 | 0.018 | 18.00 |
| Thiamine | 16.00 | 0.0308 | 0.017 | 17.00 |
| Vitamin E | 72.9 IU | 0.729 IU | 0.012 | 12.48 |
| Magnesium Sulfate | 10.00 | 0.113 | 0.113 | 113.00 |
| *Lactobacillus acidophilus | 10.00 | 0.467 | 1.418 | 1418.00 |
| Sodium Chloride | 166.00 | 0.236 | 2.368 | 2368.00 |
| Dipotassium phosphate | 116.00 | 5.85 | 1.773 | 1773.00 |
| Citric acid | 31.00 | 1.59 | 0.482 | 482.00 |
| Yeast (hydrolyzed) | 180.00 | 0.1957 | 0.283 | 283.00 |
| Glycine | 0.142 | 0.0142 | 0.142 | 141.80 |
| Potassium chloride | 18.00 | 0.93 | 0.283 | 283.00 |
| Vitamin $D_3$ | 29.00 | 0.729 | 0.002 | 1.56 |
| Dextrose | 40.00 | 2.00 | 21.38 | 21375.00 |
| Artificial flavor | 0.028 | 0.0028 | 28.548 | 28.30 |
| Transfer Factor | 50.00 | 0.05 | 0.75 | 750.00 |
| Sipernat (silicon dioxide) | | | 0.05 | 56.70 |

*$10^9$ colony forming units (CFU)/gm

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All patents, patent applications, publications, and references cited herein are expressly incorporated by reference in their entirety.

Example 1

A seven year old warm blooded Pajarro horse was urinating frequently and showing other clinical signs of pre Cushings syndrome. Morning and evening thyroid readings of 22.33 ng and 19.8 ng and insulin readings of 31.0 UIU and 43.2 UIU respectively confirmed this diagnosis. The horse was place on a daily dose of 5 ounces of the premix formulation as shown in column 5, Table 2. After seven days on the formulation the frequency of urination had greatly decreased and the horse's temperament had significantly improved. Blood studies taken 32 days after the initiation of treatment, which showed morning and evening thyroid readings of 28.4 ng and 42.7 ng and insulin readings of 40.3.0 UIU and 33.62 UIU, respectively, exhibited an improved thyroid level and cortisol rhythm.

Example 2

Two horses, one 7 years old and the other a yearling, exhibited signs of chronic dust cough, a condition that has an allergic component with increased eosinophilia. The 5 year old thoroughbred had been treated with tribrissin and an antihistamine. His intake eosinophil count was 8 and the monocyte count was 7. After being placed on 1 ounce of the stress formulation as shown in column 5, Table 5, twice daily for 14 days, the horse appeared to be in complete remission. He was then placed on a treatment of 5 ounces daily of the premix formulation as shown in column 5, Table 2. At the end of 22 days, the cough was completely eliminated and the eosinophil count was down to 3 and the monocyte count was down to 6. The yearling who had been on expensive antibiotics and cough suppressants showed no clinical symptoms of the chronic cough after receiving a daily dose of 5 ounces of the premix formulation as shown in column 5, Table 2, for 10 days.

Example 3

Two horses were received that had been positively diagnosed with Cushings disease and had previously been treated with Pergolyde and Cyrohexadine. One of the horses had initial morning and evening thyroid readings of 5.3 ng and 7.4 ng and insulin readings of 142.8 UIU and 110.2 UIU, respectively. Both horses showed dramatic improvement after days on a daily 5 ounce dosage of the premix formulation as shown in column 5, Table 2. Both horses continued with a positive response after being maintained for 2 months on the same dosage. Morning and evening blood results of thyroid readings of 70 ng and 16.1 ng and insulin readings of 110. 3UIU and 65.2UIU confirmed improvements in thyroid function and cortisol rhythm.

Example 4

The stress formulation (Table 5) was used successfully to treat two thoroughbred racehorses with chronic dust cough. After 5 days of receiving two ounces per day of the Stress formulation shown in column 5, Table 5, both horses had dramatically improved with one horse no longer showing any symptoms of the eosinophilic dust cough and the other horse showing approximately a 60% improvement over its previous symptoms.

Example 5

Three pigs with acute viral infection and temperatures of 105° were placed on one ounce daily of the Stress formulation shown in column 5, Table 5. Within 24 hours, all three pigs ate normally and exhibited normal temperatures.

Example 6

Two foals, 10 and 12 days old, suffering from diarrhea had not responded to previous treatments of antibiotics and electrolytes. Both foals were placed on one ounce of the Stress formulation as shown in column 5, Table 5, twice daily. After two days on this treatment, both foals were symptom free.

Example 7

An 80 pound golden retreiver that has reoccurring squamous cell carcinoma was given 28 grams of the canine formula as shown in column 5, Table 2, per day for 6 weeks. The 6-week administration of this formulation per day showed a 40% reduction in the tumor.

Example 8

Five cats were suffering from upper respiratory infections. They were treated with a dosage of the Stress formulation in milligrams per pound as shown in column 4, Table 5. All cats responded with remission of symptoms in three days after initiation of this treatment.

Example 9

A 16 year old gelding, Dutch warm blood was exhibiting no energy, irritability, awkward movement, a chronic girth itch and was unable to carry his head correctly. A blood test showed a low lymphocyte count of 624/uL, with 1500 to 7700/uL being normal, and also showed a marginally low T4 thyroid count of 1.0 ug/dL. He had been receiving long term treatments of Trimethoprim Sulfur, vitamins and some nutritional changes. This treatment was stopped and he was administered orally 1 oz of the stress formulation twice daily as shown in column 5 of Table 5 for a few days and showed some improvement. He was then placed on a daily oral dose of 5 oz of the premix formulation as shown in column of Table 2. After 5 days of treatment the horse was significantly improved, eating better and holding his head erect. A blood test taken seven days after the premix formulation treatment began showed that the lymphocyte count had increased to 940/uL. Approximately 35 days after treatment with the premix formulation, another blood test showed a lymphocyte count improvement to 1404/uL and a thyroid increase to 1.5 ug/dL. A normal thyroid range is 0.9 ug/dL to 2.8 ug/dL. His clinical appearance was excellent, locomotion had improved, cervical balance was better and the girth itch appeared 80 percent improved. He has remained well and is being used as a normal performance horse in three-day eventing.

Example 10

A seven year old mustang gelding with a three year duration of onchocerciasis exhibiting stomach ulceration and severe pruritus of tail and main, had been treated with conventional cortisone and antibiotics with little success. The horse was placed on a daily oral treatment of 5 oz. of the premix formulation as shown in column 5 of Table 3. After two months a blood test showed that the white blood cell counts had stabilized. After six months the thyroid level was normal, the clinical symptoms had gone and the horse was in complete remission.

Example 11

Approximately 60 young foals were suffering from severe cases of strangles also known as Strep Equi, a secondary infection of *Rhodococcus equi* and upper respiratory infections. The problem was being complicated by heat causing dehydration and also by dust. Most of the foals were also suffering from dust pneumonia. The foals had not responded to previous conventional therapy of antibiotics, of gentomycin sulfate, penicillin, amikacin. Twenty-one of the foals were first treated with one ounce of the Stress formulation shown in column 5, Table 5, twice a day for two days and then were treated with one ounce once a day for three more days. Three foals showed significant recovery after five days. These three foals were treated with one ounce of the Stress formulation described above twice a day and no antibiotics. Two of the foals that had just contracted the disease responded immediately in 48 hours showing very little coughing, clear nostrils and increased appetite. The other foal had to be placed on antibiotics in addition to the Stress formulation and responded in five days with supportive antibiotics. The remaining 18 diseased foals with strangles and upper respiratory ailments received one ounce twice daily of the Stress formulation in column 5, Table 5 for two days and then received one ounce daily of the same Stress formulation for the next 8 days. Blood tests were initially taken on these foals and again ten days after treatment began.

About 14 of these remaining foals showed a marked improvement after 10 days with no antibiotics. The initial blood results show elevated neutrophil and monocyte counts on the majority of the foals with high band cell counts. Foals with early signs of the strep equi infection showed depressed lymphocyte counts. After ten days of treatment blood results showed normalization of the differential of neutrophils, lymphocytes, and monocytes. The most significant finding was total reduction of band cells in all but one foal. Platelet cells were increased in practically all foals.

Reduction of band cells is indicative of a powerful immune response. The platelet cell increase may be from stimulation of stem cells. Hydration improved from the electrolyte and probiotic combination with transfer factor. Also, as an adjunct to antibiotic therapy, the stress formula appeared very beneficial and in early onset of disease the stress formula appeared to boost the immune response to the extent that antibiotic therapy may not be necessary.

The problem with treating strangles with antibiotics is that for some reason antibiotics allow the "Strep equi" organism to lie dormant causing a disease of bastard strangles later in life in that lymph nodes containing the bacteria can show up at any age and create a chronic illness or acute death.

Example 12

This case involved dairy drop calves. These calves usually receive very little colostrum if any and, upon arrival at the farm, frequently break with shipping fever symptoms, the term used for generalized viral infections, upon arrival at the farm. These symptoms usually last ten days with conventional antibiotic therapy and result in a high mortality rate. However, the disease also often leaves permanent scarring of the lungs and gastrointestinal tract which leaves poor producing dairy cows. Ten of the calves received one ounce daily of the Stress formulation as set forth in column 5, Table 5, for four days and then one half ounce of that formulation for the next three days. The ten controls received no Stress formulation. After 7 days, one of the Stress formulation treated calves contracted shipping fever and had to be treated with antibiotics. Out of the 10 controls, 7 calves had to be treated with antibiotics. The overall test showed a 60 to 80 percent reduction in morbidity.

Example 13

A 10 year old 70 pound golden retriever suffering with a squamous papilloma of the eyelid of a clinical size of about 1 cm in length, received surgery to remove the tumor. Within two months the tumor had reoccurred and had grown rapid rapidly again to 1 cm. The retriever was placed on a daily dosage of 28 grams of the canine formula as shown in column 5, Table 3. After 60 days on this dosage of the canine formula, not only had the tumor stopped growing but the size of the tumor was reduced by 30%.

Example 14

A 1000 pound horse was suffering from scratches. Scratches is a bacterial, fungal infection of the rear legs consisting of staphilococcus and Trichophyton mentagreophytes. After 7 days of receiving 1 ounce twice daily of the stress formulation as shown in column 5, Table 5, the infection on the rear legs had improved at least 50% and the swelling and sores that had occurred were greatly reduced.

Example 15

A nine year old thoroughbred cross, gelding, performance horse exhibited clinical signs of Cushing's syndrome, including heavy breathing, ulcers around the coronet band and hypothyroidism. He had previously been treated with Azium, Ventipulium, prednisone and broncodilators but showed no improvement. A daily treatment of approximately 5 oz. of the premix formulation as set forth in column 5 of Table 2 showed some improvement. After the addition of 750 mg of transfer factor to the above Premix dosage, all given daily, the horse showed immediate and significant improvement in it's performance. The horse continued to improve and after being kept on the same transfer factor and premix formulation, the horse recovered completely. When the horse was taken off the transfer factor and premix, he relapsed but recovered after being placed again on the same transfer factor and premix formulation again.

Example 16

A 1,000-pound gelding suffering from onchoceriasis as exhibited by skin thickness and other symptoms is administered 750 mg of transfer factor, 500 mg of total zinc and 2 gm of flax seed oil. The onchoceriasis symptoms are reduced as exhibited by a 60% reduction in skin thickness.

Example 17

A 1000 pound horse with a temperature of 103° F. is given 750 mg of transfer factor, 500 mg of total zinc, 2 gm of Flax seed oil, 7 gm of hydrolyzed yeast and 1.5 gm of Vitamin C. The horse shows a reduced temperature of approximately 100.5° F. within 48 hours.

Example 18

A 1000 pound gelding exhibiting a low lymphocyte count is given a daily dosage of 750 mg of transfer factor, 500 mg of total zinc, 2 gm of Flax seed oil, 7 gm of hydrolyzed yeast, 1.5 gm of Vitamin C, 2 gm of methyl sulfonyl methane, 15 mg of arginine and 1103.86 mg of methionine. After being given this dosage for 30 days, the lymphocyte count of the gelding is increased 30%.

Example 19

A colt weighing 1000 pounds with a bacterial infection with a minor cut on the leg and a temperature of 105° is given 750 mg of transfer factor and 2.35 gm of lactobacillus acidophilus. With 48 hours after administration of this composition, the temperature is reduced to 101° F. and the swelling is reduced approximately 50%.

Example 20

A 3-year old 1000 pound colt having a respiratory infection that is viral in origin with a temperature of 104° responds to 750 mg of transfer factor, 2.3 gm of lactobacillus acidophilus, 500 mg of zinc and 3 gm of yeast given daily by showing a reduction in temperature to approximately 101.5° F. and improved breathing within 72 hours following the initiation of this treatment.

Example 21

A 1000 pound horse with hoof separation from white line disease and micro absecessation responds to a daily dosage of 750 mg of transfer factor, 2.3 gm of lactobacillus acidophilus, 500 mg of total zinc, 3 gm of yeast and 24.12 gm of montmorillinite. After 90 days of treatment the horse shows improved hoof growth of approximately 1cm and approximately a 60% reduction of white line disease or absecessation.

Example 22

A 1000 pound gelding with Cushings disease is fed 5 ounces daily of the premix formulation shown in column 5, Table 2, except that the horse receives 3 gm of Flax seed oil and no canola oil or safflower oil. With 30 days of continuous treatment at this dosage, the clinical symptoms of frequent urination, low blood sugar and low alertness are improved approximately 30%. With 90 days at this treatment, the Cushings symptoms are 50% reduced.

Example 23

A 15-pound cat with flea bite dermatitis is treated with 250 mg of transfer factor, 108 gm of lactobacillus acidophilus for 10 days and showed a 40% improvement in arithmic ulcerations of the skin caused by the flea bites.

Example 24

A 15 pound cat with reddened skin under the stomach and partial hair loss from flea bite dermatitis and possibility autoimmune or atopic dermatitis is treated daily with 250 mg of transfer factor, 37 mg of lactic acid bacteria, 72 mg of hydrolyzed yeast, 7.78 mg of zinc and 37.6 mg of montmorillinite for 10 days. The clinical symptoms of reddened skin and hair loss at the end of this time are reduced approximately 50%.

Example 25

A 15 pound cat tests positive to feline leukemia virus. With 60 days treatment of a daily dose of 250 mg of transfer factor, 37 mg of lactobacillus acidophilus, 7.78 mg of zinc and 72 mg of hydrolyzed yeast, the cat is no longer exhibiting clinical symptoms of feline leukemia virus and the laboratory tests are negative.

Example 26

A 15 pound cat with flea bite dermatitis is treated daily with 250 mg of transfer factor, 37 mg of lactobacillus acidophilus, 72 mg of hydrolyzed yeast and 37.6 gm of montmorillinite. Within 7 days of daily treatment, the ulcerations occurring from the flea bite dermatitis are at least 40% reduced.

Example 27

One day old drop dairy calves weighing 100 pounds each with shipping fever exhibiting clinical symptoms of poor appetite, diarrhea and an elevated fever are administered a daily dosage in their food of 375 mg of transfer factor, 709 mg of lactobacillus acidophilus, 14 mg of calcium pantothenate, 56.5 mg of a chelated magnesium, 1158 mg of a sodium salt, 141 mg of a potassium salt and 881 mg of a phosphate. Within 4 days of receiving this treatment, the morbidity rate in the calves is reduced 50% as compared to controls.

Example 28

Ten pigs each weighing 10 pounds and exhibiting elevated temperatures and slightly loose stool are administered 250 mg of transfer factor, 467 mg of lactobacillus acidophilus, 9.24 mg of calcium pantothenate, 37 mg of magnesium, 781 mg of a sodium salt, 93 mg of a potassium salt and 585 mg of phosphorus in the form of dipotassium phosphate along with 15 mg of citric acid daily. These pigs exhibit a 50% reduction in morbidity within 5 days of administration of this formulation in comparison to controls that do not receive the formulation.

Example 29

Ten show chickens weighing 10 pounds each show signs of elevated temperature, distress from shipping fever complex that is viral in origin, poor appetite and lethargy. A daily dosage of 250 mg of transfer factor, 467 mg of lactobacillus acidophilus, 924 mg of a chelated calcium pantothenate, 37 mg of a magnesium sulfate, 781 mg of a sodium salt, 93 mg of a potassium salt, 585 mg of dipotassium phosphate, 159 mg of citric acid, 4.62 mg Vitamin A, 5.4 mg Vitamin $B_2$, 65.3 mg Vitamin $B_{12}$, 5.8 mg Vitamin C and 4.1 mg Vitamin E daily in their drinking water reduces morbidity 50% within 72 hours as compared to a control group that does not receive this treatment.

Example 30

Five horses weighing approximately 500 pounds each with Strangles as exhibited by snotty noses, elevated temperatures and swollen lymph nodes are administered 750 mg of transfer factor, 1.42 gm of lactobacillus acidophilus, 28 mg of calcium pantothenate, 113 mg of magnesium sulfate, 2368 mg of sodium chloride, 283 mg of potassium chloride, 1773 mg of dipotassium phosphate, 482 mg of citric acid along with 14 mg Vitamin A, 18 mg Vitamin $B_2$, 17 mg Thiamine, 1,56 mg Vitamin $D_3$, 17 mg Vitamin C and 12.48 mg Vitamin E, twice daily. The morbidity rate for these horses is reduced 50% as shown by a 50% reduction in symptoms when compared to a control group not receiving the above formulation. Chronic abscessation is eliminated approximately 40% again when compared to a control group not receiving the above formulation.

Example 31

A 1000 pound horse with a flat sarcoid in the ear tip is given 5 ounces of the premix formulation as shown in column 5 of Table 2 daily for 60 says. At the end of the 60-day treatment, the sarcoid is reduced 30% in size.

Example 32

A serious outbreak of mycoplasma occurs in 20 goats exhibiting symptoms of ocular and nasal discharge. The milking goats are also suffering mastitis as a result of the disease. The goats are given 1 ounce daily of the stress pak formulation shown in column 5, Table 4, for 7 days. A 40% improvement in the clinical symptoms of the mycoplasma is seen with administration of this stress dosage.

Example 33

A 1000 pound warmblooded horse having equine protozoal myelitis is treated daily for four weeks with 5 ounces of the premix formula as shown in column 5, Table 2, in addition to traditional medication such as pyrimethamine and sulfadiazine. This treatment produces a 50% improvement in symptoms.

Example 34

A 1000 pound Arabian horse having a one inch melanoma situated below the tail head and growing at ½ inch per 6 months is treated for 60 days with 5 ounces daily of the premix formulation as shown in column 5, Table 2. This treatment stops the growth of the melanoma and reduces the size of the tumor about 20%.

What is claimed is:

1. A method of treating Cushings syndrome, Cushings disease, a benign tumor, onchoceriasis, hypothyroidism, or equine protozoal myelitis (EPM) in an animal comprising administering to the animial a formulation comprising pharmaceutically acceptable transfer factor, zinc and at least one pharmaceuticaly acceptable essential fatty acid in an amount, at a frequency and for a duration effective to reduce or eliminate said tumor or symptoms of said Cushings disease or syndrome, onchoceriasis, hypothyroidism, or equine protozoal myelitis.

2. A method of treating Cushings syndrome, Cushings disease, a benign tumor, onchoceriasis, hypothyridism, or equine protozoal myelitis in a an comprising administering to the animal a formulation comprising pharmaceutcally acceptable transfer factor, zin, at least one pharmaceutically acceptable essential fatty acid, Vitamin C and pharmaceutically acceptable yeast in an amount, at a frequenc and for a duration effective to reduce or eliminate said tumor or symptoms of said Cushings disease or syndrome, onchoceriasis, hypothyroidism, or equine protozoal myelitis.

3. A method of treating Cushings syndrome, Cushings disease, a benign tumor, onchoceriasis, hypothyroidism, or equine protozoal myelitis in an animal comprising administerinlg to the animal a formulation comprising pharmaceutically acceptable transfer factor, zinc, at least one pharmaceutically acceptable essential fatty acid, Vitamin C, pharmaceutically acceptable yeast and pharmaceutically acceptable ionic salts or chelates of calcium, phosphorous, selenium, iron, magnesium, manganese, copper, iodine, cobalt and molybdenum in an amount, at a frequency and for a duration effective to reduce or eliminate said tumor or symptomas of said Cushings disease or syndrome, onchoceriasis, hypothyroidism, or equine protozoal myelitis.

4. A method of treating Cushings syndrome, Cushings disease, a benign tumor, onchoceriasis, hypothyroidism, or equine protozoal myelitis in an animal comprising administering to the animal a formulation comprising pharmaceutically acceptable transfer factor, zinc, at least one pharmaceutically acceptable essential fatty acid, Vitamin C, pharmaceutically acceptable yeast, pharmaceutically actable ionic salts or chelates of calcium, phosphorous, seleniudi, iron, magnesium, manganese, copper, iodine, cobalt and molybdenum, pharmaceutically acceptable lactic acid generating bacteria, yeast, montnorillonfite and Vitamins A, $B_2$, $B_6$, $B_{12}$, E and K in an amount, at a frequency and for a duration effective to reduce or eliminate said tumor or symptoms of said Cushings disease or syndrome, onchoceriasis, hypothyroidism, or equine protozoal myelitis.

5. A method of treating Cushings syndrome, Cushings disease, a benign tumor, onchoceriasis, hypothyroidism, or equine protozoal myelitis in an animal comprising administering to the animal a formulation comprising phamaceutically acceptable transfer factor, zinc, at least one pharmaceutically acceptable essential fatty acid, Vitamin C, pharmaceutically acceptable yeast, pharmaceutically acceptable ionic salts or chelates of calcium, phosphorous, selenium, iron, magnesium, manganese, copper, iodine, cobalt and molybdenum, pharmaceutically acceptable lactic acid generating bacteria, yeast, montmorillonite, Vitamins A, $B_2$, $B_6$, $B_{12}$, E and K, pharmaceutically acceptable d-biotin, folic acid, niacin, Vitamin $D_3$, pantothenic acid and thiamine in an amount, at a frequency and for a duration effective to reduce or eliminate said tumor or symptoms of said Cushings disease or syndrome, onchoceriasis, hypothyroidism, or equine protozoal myelitis.

6. A method of treating Cushings syndrome, Cushings disease, a benign tumor, onchoceriasis, hypothyroidism, or equine protozoal myelitis in an animal comprising administering to the animal a formulation comprising pharmaceutically acceptable transfer factor, zinc, at least one pharmaceutically acceptable essential fatty acid, Vitamin C, phanmaceutically acceptable yeast, pharmaceutically acceptable ionic salts or chelates of calcium, phosphorous, selenium, iron, magnesium, manganese, copper, iodine, cobalt and molybdenum, pharmaceutically acceptable lactic acid generating bacteria, yeast, montnorillonite, Vitamins A, $B_2$, $B_6$, $B_{12}$, E and K, pharmaceutically acceptable d-biotin, folic acid, niacin, Vitamin $D_3$, pantothenic acid, thiamine, pharmaceutically acceptable lysine, methionine, arginine and methyl sulfonyl methane in an amount, at a frequency and for a duration effective to reduce or eliminate said tumor or symptoms of said Cushings disease or syndrome, onchoceriasis, bypothyroidisin, or equine protozoal myelitis.

* * * * *